United States Patent
Mandl et al.

(10) Patent No.: US 10,426,636 B2
(45) Date of Patent: Oct. 1, 2019

(54) ARTIFICIAL FINGER

(71) Applicant: OTTO BOCK HEALTHCARE PRODUCTS GMBH, Vienna (AT)

(72) Inventors: Clemens Mandl, Vienna (AT); Leopold Oecker, Vienna (AT); Richard Skiera, Vienna (AT); Johannis Willem Van Vliet, Vienna (AT); Ronald Naderer, Oberneukirchen (AT); Paolo Ferrara, Kematen an der Krems (AT); Florian Schausberger, Linz (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 0 days.

(21) Appl. No.: 14/786,506

(22) PCT Filed: Apr. 29, 2014

(86) PCT No.: PCT/EP2014/001143
§ 371 (c)(1),
(2) Date: Oct. 22, 2015

(87) PCT Pub. No.: WO2014/177272
PCT Pub. Date: Nov. 6, 2014

(65) Prior Publication Data
US 2016/0089251 A1 Mar. 31, 2016

(30) Foreign Application Priority Data

May 3, 2013 (DE) .......................... 10 2013 007 539

(51) Int. Cl.
A61F 2/54 (2006.01)
A61F 2/58 (2006.01)
A61F 2/78 (2006.01)

(52) U.S. Cl.
CPC ...... *A61F 2/586* (2013.01); *A61F 2002/7887* (2013.01)

(58) Field of Classification Search
CPC .... A61F 2/54; A61F 2/58; A61F 2/586; A61F 2002/7887; A61F 2002/30561
See application file for complete search history.

(56) References Cited

U.S. PATENT DOCUMENTS 5,108,140 A * 4/1992 Bartholet ............ B25J 15/0009
294/106
5,108,443 A 4/1992 Branemark
(Continued)

FOREIGN PATENT DOCUMENTS

CN 101014304 A 8/2007
CN 101321508 A 12/2008
(Continued)

OTHER PUBLICATIONS

PCT International Search Report for PCT International Patent Application No. PCT/EP2014/001143, dated Oct. 28, 2014.

*Primary Examiner* — Bruce E Snow
(74) *Attorney, Agent, or Firm* — Holland & Hart, LLP

(57) ABSTRACT

An artificial finger for prosthetics and gripping technology, with a base, a first finger member mounted on the base in articulated manner, at least one secondary member mounted on the first finger member in articulated manner, and a drive for adjusting the secondary member relative to the first finger member and the first finger member relative to the base. At least one reset element is provided for resetting the first finger member and the secondary member, and the first finger member is acted upon with a resetting force which differs from the secondary member.

17 Claims, 8 Drawing Sheets

(56) References Cited

U.S. PATENT DOCUMENTS

| | | | | |
|---|---|---|---|---|
| 5,762,390 | A | * | 6/1998 | Gosselin ................ B25J 15/103 |
| | | | | 294/106 |
| 6,244,644 | B1 | | 6/2001 | Lovchik et al. |
| 6,896,704 | B1 | | 5/2005 | Higuchi et al. |
| 7,922,773 | B1 | * | 4/2011 | Kuiken .................... A61F 2/54 |
| | | | | 623/24 |
| 2007/0213831 | A1 | | 9/2007 | Cubber |
| 2012/0109337 | A1 | | 5/2012 | Schulz |

FOREIGN PATENT DOCUMENTS

| | | |
|---|---|---|
| CN | 201861802 U | 6/2011 |
| DE | 320702 | 4/1920 |
| DE | 2426711 A1 | 9/1975 |
| DE | 2925225 A1 | 1/1981 |
| DE | 60023142 T2 | 7/2006 |
| EP | 0045818 A1 | 2/1982 |
| GB | 108872 A | 8/1917 |
| SU | 971313 A1 | 11/1982 |
| WO | 2010/018358 A2 | 2/2010 |
| WO | 2010/051798 A1 | 5/2010 |
| WO | 2011/087382 A1 | 7/2011 |
| WO | 2011081851 A3 | 9/2011 |

* cited by examiner

ARTIFICIAL FINGER

TECHNICAL FIELD

The invention relates to an artificial finger with a base, a first member mounted on the base in an articulated manner, at least one secondary member mounted on the first finger member in an articulated manner, and a drive for adjusting the secondary member relative to the first finger member and the first finger member relative to the base.

BACKGROUND

Artificial fingers are used in prosthetics and also in handling technology, where robots or handling systems are equipped with finger-bearing grippers. In use on prosthetic hands, prosthetic fingers are needed to functionally or visually replace missing fingers of a natural hand. For robots or handling systems, artificial fingers should simulate the flexibility of the human hand. In the present description, both technical gripping elements and also prosthetic components are meant when speaking generally of fingers, otherwise the nature of the fingers is specifically indicated. Gripping mechanisms are understood to be both prosthetic hands and also technical grippers, end-effectors and handling mechanisms. Aside from passive prosthetic fingers, which predominantly have a cosmetic function and which are mounted on a base in a non-actuating manner, it is necessary to actuate fingers to actuate relative to a base in order provide a gripping mechanism with which objects can be gripped. In the simplest case, a rigid finger is mounted in an articulated manner on the base and coupled to a cable system which causes flexion against a resetting spring during actuation.

Many different actuating mechanisms for prosthetic fingers are known from WO 2010/018358 A2. In addition to cables, which can be operated directly via motors fixed on the base or which are fixed on a movable yoke, direct drives for displacement of the proximal members relative to the base by means of gears or spindles are disclosed. In addition, a coupling of a secondary member to a proximal member via a separate band element is shown, so that an automatic flexion of the secondary member is made during a flexion of the proximal member.

DE 600 23 142 T2 relates to a movable finger for a prosthesis with a base in which a drive is mounted. A flexion of an intermediate portion may occur via a wire, which is attached to a spindle nut; resetting when the drive is reversed is undertaken by means of an intermediate portion spring. A plurality of distal members may be bent via a cable system.

WO 2011/087382 A1 relates to a modular prosthetic hand with mechanically independent finger modules, in which an electric motor with a gear is arranged within a proximal section of the finger. Via a multi-link system, a distal element can be pivoted relative to a proximal element upon adjustment of a worm gear, while at the same time a force is transferred via a coupling rod in order to pivot the proximal element relative to the base.

SUMMARY

The object of the present invention is to provide an artificial finger which, with a simple construction, enables an improved application to an object to be gripped and which is versatile in use.

According to the invention, this object is achieved by an artificial finger with the features of the main claim and the features of the additional independent claim. Advantageous embodiments and developments of the invention are disclosed in the dependent claims, the description and the figures.

In the artificial finger according to the invention with a base, a proximal member mounted on the base in articulated manner, at least one secondary member mounted on the first finger member in articulated manner, and a drive, in particular a motor drive, for adjusting the secondary member relative to the first finger member and the first finger member relative to the base, provision is made that at least one reset element is provided for resetting the first finger member and the secondary member, and the first finger member is acted upon with a resetting force which differs from the secondary member. By acting upon the finger members with different resetting forces, it is possible to achieve a coordinated bending and resetting behavior of the artificial finger, which is particularly advantageous for underactuated fingers, as the desired behavior can be achieved with little effort and only one drive. It is not necessary for a plurality of drives to be provided in order to generate a contact or release of the fingers on the objects to be gripped.

In a variant of the invention, the reset element is coupled to a force transmission mechanism or is formed as a spring element with differing spring constants over the length of the spring element. The force transmission mechanism may be designed as a lever, lever system, gears, cable construction with roll-up gear, friction gear or the like. Alternatively to the equipping with a force transmission mechanism, which divides the gripping and resetting force differently on the individual finger members, the reset element or the force accumulator, which works against the drive, may be formed as a spring element which has differing spring constants along its length, so that, at different locations on the spring element, different resetting forces are effected which act against the drive force in order to enable a stepped applying or releasing of individual finger members. The spring element may be formed for example as a flexible rod made from metal or plastic with differing cross sections along its length in order to create locally differing resetting forces.

In a variant of the invention, a first resetting spring provides the secondary member with resetting forces in relation to the first finger member and a second resetting spring provides the first finger member with resetting forces in relation to the base in the direction of a starting position, wherein the spring constants of the resetting springs are different. In this way, it is possible to generate a differential kinematic with little effort, in which two degrees of freedom are realized with a single drive, said degrees of freedom ensuring the greatest possible gripping safety independently of the geometry of the object to be gripped and at the same time leading to a physiological gripping pattern in use as a prosthetic finger.

In a development of the invention, the spring constant of the first resetting spring is greater than the spring constant of the second resetting spring, so that a pivoting of the secondary member relative to the first finger member requires application of a greater force than a pivoting of the first finger member relative to the base. It is thereby achieved that the finger is first pivoted about the base hinge, i.e. about the pivot axis between the first finger member and the base, and it is only when the first finger member lies against an object or against an end stop that the displacement of the secondary member relative to the first finger member begins, i.e. a flexion about the pivot axis between the first finger member and the secondary member. Thus, by means of a simple force transmission kinematic, a differential effect about at least two hinge mechanisms takes place, so that the at least two finger members can be sequentially actuated.

A traction means, in particular a belt, band or cable or a highly flexible wire, can be coupled to the drive, said traction means being fixed in turn on the base. It is thus possible to actuate a plurality of joints via a highly flexible cable, with a simple kinematic with only one drive, in a force-controlled manner which is dependent on the gripping situation.

Here, the traction means may be guided around the pivot axis of the secondary member, in order to be applied to at least one force application point beyond the pivot axis of the secondary member, which leads to a stable execution of the traction means with a simultaneously reduced friction. It is also provided that the traction means is guided below the distal pivot axis, so as to effect a simple and direct application of the pulling force for pivoting the secondary member. Advantageously, the traction means is guided on the secondary member about at least one deflection mechanism, for example a deflection roller or a pin with a low coefficient of friction, so that the drive power is not converted, or is converted as little as possible, into frictional energy.

The deflection mechanism may be mounted displaceably or pivotably on the secondary member, for example on a pivot arm or in a slot or elongated hole guide, via which it is possible to achieve a compensation of play across a predetermined path. Insofar as the traction means and in particular the deflection mechanism are subjected in the distal direction to a pre-tensioning force, there arises a basic pre-tensioning of the traction means between the drive and the fixing point at the base, so that an overload protection is present if, for example, the secondary member is unintentionally flexed and extended after application of an impact load. By means of the pre-tensioning force, the finger can be used again immediately. In the case of an undesired flexion, for example due to an impact load, no forces are transferred via the traction means to the drive, whereby an overload protection is achieved through force decoupling. The extension beyond the zero position, so-called hyperextension, may also be used advantageously for gripping flat objects.

The drive can be formed as a self-locking linear drive, so that after reaching a desired position, which can be detected, for example, via a sensor, no additional power consumption is required to maintain the adjusted position of the secondary member and/or of the first finger member. In principle it is also possible and provided that the drive is not formed as a self-locking electric motor, but rather for example as a pneumatic actuator which is not self-locking. In such an embodiment, an action of force is still present at the existing pressure, even with locked valves, however there is no consumption of air. Pneumatic actuators are particularly suitable for maintaining the gripping force. Drives which are not self-locking also offer the advantage of overload protection. Opposing forces are absorbed only up to a certain limit, above which the drives yield, as a result of which the drive train cannot be loaded beyond this limit. If a self-locking drive is provided, an overload mechanism is advantageous. Additionally, drives which are not self-locking also fulfill the function of a tensioner in the case of an active force control, as the drive always pulls on the traction means or cable with the set force, so that said traction means or cable cannot slacken.

The drive may have a reduction gear, which is coupled to a roller or spindle gear, on which the traction means is in turn fixed, so that small, high-speed motors, in particular external rotor motors, can be used, which enable with a corresponding reduction a precise yet powerful displacement of the secondary member and first finger member. The drive may roll the traction means onto a roll, for instance a pre-tensioned roll, or fix it on a spindle nut via a spindle gear, so that the traction means is actively released on reversal of the rotational direction.

The drive may be arranged both in the first finger member and also in the secondary member; in principle it is also possible that the drive be arranged within a base element, for example in the metacarpal region of a prosthetic hand. In handling devices, this embodiment corresponds to a separation of the gripping module into a drive component and a gripping kinematic. The part of the gripping module designated as the gripping kinematic converts the movement of an actuator into a movement of the fingers or the active elements. It is also possible that several drives are arranged in the finger elements, to enable a multi-stage, individual displacement. It is thus possible to produce a finger which, in addition to a positioning of a first finger member or proximal member on a base, e.g. metacarpal base, also has a medial member and a secondary member, wherein a drive is arranged both in the first finger member and also in the medial member. The medial drive is thus the first finger member for the secondary member. In an embodiment with two finger joints, it is also possible to extend the drive of the traction means beyond a first secondary member, which is then a medial member, to the secondary member and to provide a stepped configuration of the spring rates for the resetting springs into the starting position. It may be provided here that the resetting spring for the first finger member has a lower spring rate relative to the base than the resetting spring for the medial member to the first finger member, which is in turn lower than the spring rate of the resetting spring between the medial member and the secondary member. It is also possible and provided, in an embodiment with two secondary members, that only a single drive is provided, which is mounted in the first finger member or on the base, and which causes a flexion of the members upon corresponding actuation. In all cases, an underactuated system is present with fewer actuators than degrees of freedom.

The first finger member and/or the secondary member may be mounted so as to be hyperextendable, so that it is possible that the respective finger member be extended beyond the normal extended position, in which in general the longitudinal axes of the finger members are aligned. Further, it is provided that the switching point of the force application between flexion and extension is arranged in the extendable or hyperextendable finger member and/or secondary member, wherein the force introduction point for the displacement of the finger member is displaceable, so that, in a corresponding displacement of the force introduction, a switching from extension to flexion may take place, so that two movements may be executed by means of the artificial finger, according to the positioning of the force application, without changing the force direction in the traction means. The force introduction point can be altered in different ways, for example force-controlled by elastically mounted deflection elements, which are displaced by the force within the traction means. It is also possible to provide switching mechanisms such as levers, sliders or the like, in order to position the force introduction point on this or that side of the switching point by means of displacement or rotation or shifting of deflection elements or guides of the traction means, and to achieve a correspondingly different displacement direction of the respective finger member. The displacement of the deflection elements or guides may also be affected by a motor. In principle, it is also possible and provided that the displacement of the force introduction point on this side or that side of the switching point also occurs independently of the possibility of a hyperextension, so that a directional reversal of the finger members may also be carried out actively in underactuated systems.

Mechanisms for osseointegrated mounting of the prosthetic finger may be arranged on the base or the first finger member, so that, due to the self-contained embodiment of the prosthetic finger with an integrated drive, an active, osseointegrated finger prosthesis can be realized.

An alternative provides that mechanisms for fixing on robots or handling devices are arranged on the base or the first finger member, so that the artificial fingers can be used not only in prosthetics but also in handling technology. The fixing mechanisms required for this purpose differ from the mechanisms for osseointegrated mounting, in particular they may be made more stable and larger in order to be able to transmit greater forces, and biocompatibility need not be ensured.

In an artificial finger as a prosthetic finger with a base, a first finger member mounted on the base in an articulated manner, at least one secondary member mounted on the first finger member in an articulated manner, and a motor drive for adjusting the secondary member relative to the first finger member and the first finger member relative to the base, provision is made that mechanisms for osseointegrated mounting of the prosthetic finger are arranged on the base, whereby an active prosthetic finger, which can be controlled based on electromyographic pulses, can be made available. It is also possible in principle to provide a direct coupling of a control device to neural pathways, so that an almost complete functional replacement of a lost or absent natural finger can be ensured. The technical configuration of such a prosthetic finger may correspond to the configuration described above in connection with artificial fingers, wherein all advantages and variants of the above-described configuration of the prosthetic finger can also be realized for an osseointegrated variant. All embodiments and variants described above thus also relate expressly to osseointegrated prosthetic fingers.

An exemplary embodiment of the invention is explained hereinafter in detail with reference to the accompanying figures.

DETAILED DESCRIPTION

Figure 1:
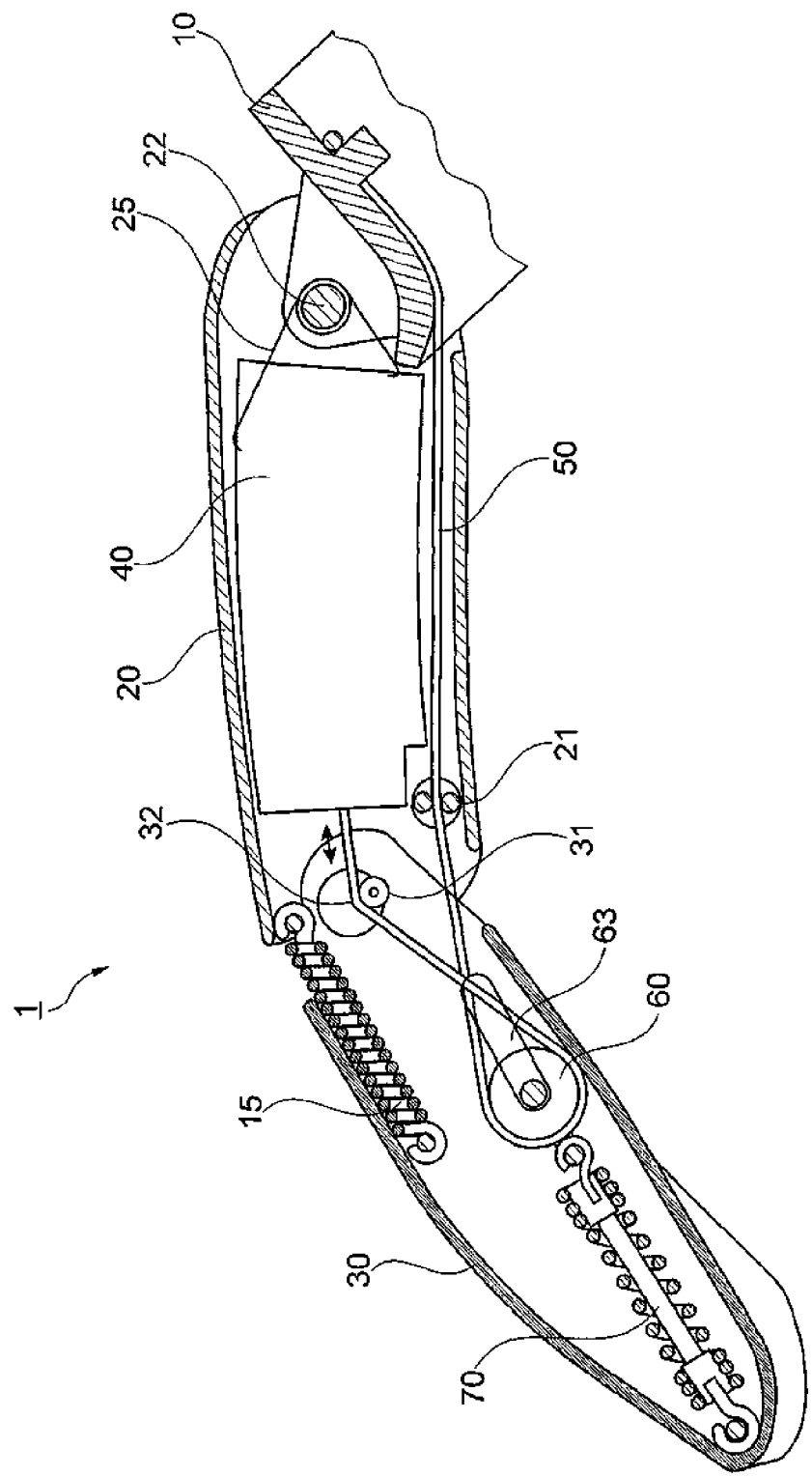
FIG. 1 shows a schematic cross-sectional view of a prosthetic finger.

FIG. 1 shows a schematic cross-sectional view of a finger 1 with a base 10 and a proximal member 20 arranged thereon and pivotable about a hinge axis 22. A pivot axis 32 is provided at the distal end of the first finger member 20 for a secondary member 30 mounted pivotally thereabout.

The base 10 may be formed as a metal plate or osseointegratable component, which can be implanted, for example, in a metacarpal bone.

Figure 1A:
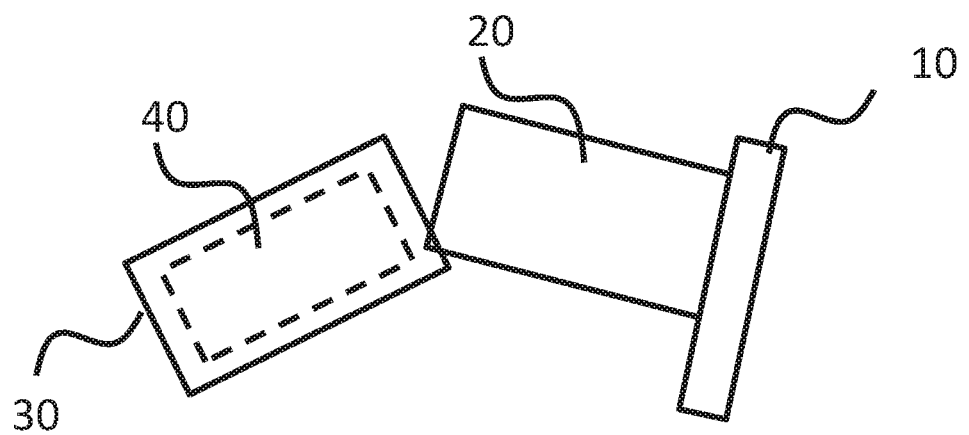
FIG. 1A shows a schematic side view of a prosthetic finger.

The proximal member 20 is hollow in the embodiment shown and has a motor drive 40 in its interior, which will be explained later in more detail. FIG. 1a schematically illustrates an alternative embodiment in which the motor drive 40 is positioned in the secondary member 30. A traction means 50, fixed on the drive 40, protrudes from a distal end of the drive 40 and can execute an alternating movement in the longitudinal extent of the first finger member 20, as is shown by the double arrow. The traction means 50, which may be designed as a belt, fiber part, stranded wire, plastic filament, string or flexible wire, is guided over a roller 31 about the pivot axis 32 and looped around a deflection element 60, which is spaced distally from the pivot axis 32 and mounted in the secondary member 30. The deflection element 60 is formed in the shape of a deflection roller, which is displaceably mounted in a slot guide 63 in the secondary member 30. The deflection roller 60 is pre-tensioned in the direction of the distal end of the secondary member 30 by means of a tension spring 70, so that the traction means 50 is always subjected to a slight pre-tensioning. This makes it possible to compensate for relative displacements of the secondary member 30, to the first finger member 20 and which occur during use are not provided by the drive 40 or resetting forces and to permit hyperextension.

The construction of the finger 1 with the overload protection is based on the fact that the tension spring 70 is pre-tensioned such that the deflection roller 60 begins to migrate within the slot guide 63 only at a certain tension, i.e. from a certain tensile load in the traction means 50, in the direction of the first finger member 20, wherein the spring force is adjusted such that the components cannot be adversely affected due to an overload. The finger 1 can thus also be opened, i.e. the secondary member 30 can extend during overload. The tension spring 70 is therefore designed to be relatively rigid and provided with a pre-tensioning, which absorbs the obtained maximal gripping force without increasing the length of the spring.

The traction means 50 loops around the deflection roller 60 and is guided by means of a cable guide 21, which is mounted on the first finger member 20, in the vicinity of the outer wall of the first finger member 20, so that the course of the traction means 50 extends substantially parallel to the housing wall.

A first resetting spring 15 is arranged between the first finger member 20 and the secondary member 30, said resetting spring 15 counteracting a flexion of the secondary member 30 relative to the first finger member 20 due to the shortening of the effective length of the traction means. In the embodiment shown, the first resetting spring 15 is formed as a tension spring, which is fixed at one end to the first finger member 20 and at the other end to the secondary member 30.

A torsion spring 25 is arranged on the first finger member 20 about the pivot axis 22 and serves as a second resetting spring 25, which causes a resetting force against a pivoting movement of the first finger member 20 relative to the base 10, so that the first finger member bears against a stop in the extended position at a maximum length of the traction means. The spring rate of the second resetting spring 25 here is lower than the spring rate of the first resetting spring 15, so that, upon a shortening of the effective length of the traction means, i.e. upon a pulling in of the traction means 50 into the drive 40, pivoting first takes place about the joint that provides less resistance, thus in the present embodiment first about the joint between the base 10 and the first finger member 20 about the pivot axis 22. Only after a resistance is reached, for example when the first finger member 20 is placed on an object, the resistance force increases up to a value above the resetting force of the first resetting spring 15, which then leads to a flexion of the secondary member 30 about the pivot axis 32 upon a further shortening of the effective length of the traction means. If the drive 40 is operated in the opposite direction, the effective length of the traction means is extended, for example by the traction means 50 being unrolled from a roller or a spindle nut being displaced distally. The secondary member 30 is then displaced firstly in an extension direction, and the first finger member 20 is displaced in the extension direction only after an extension stop for the secondary member 30 is reached.

Figure 2:
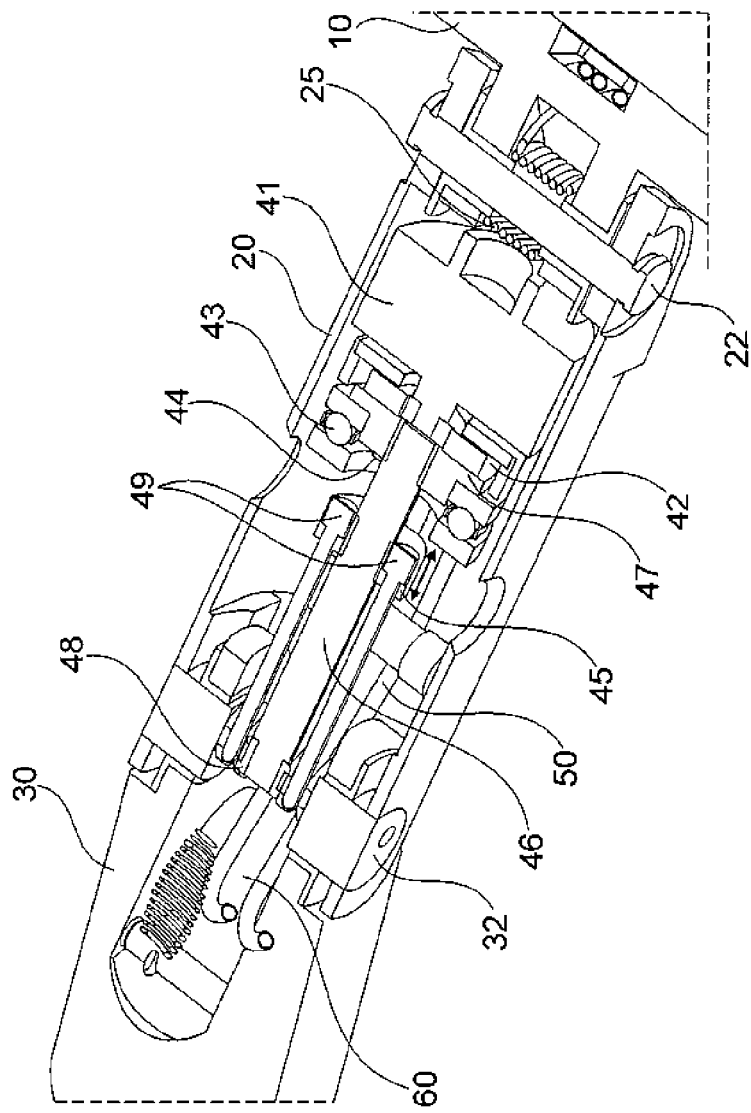
FIG. 2 shows a detailed representation of a drive.

FIG. 2 shows a detail view of the drive 40 with a high-speed motor 41, which is formed as an external rotor motor. In the installed state, the external rotor motor 41 connects distally to a planetary gear stage 42, the planetary carrier 47 of which is part of a motion screw 46. The planetary carrier 47 is supported via an axial ball bearing 43 on a housing, not shown further. A spindle nut 45 is arranged on the motion screw 46, on which spindle nut 45 the traction means 50 is fixed in the form of two cables or wires on mountings 49 positioned on both sides of the motion screw. This is supported in a bearing 48, for example a sliding bearing or roller bearing, at the distal end of the motion screw 46. Limit switches 44 are arranged at the respective end areas of the motion screw 46, of which only the limit switch at the distal stop is shown, via which the external rotor motor 41 is switched off when the maximum travel distance of the spindle nut 45 has been reached. Further movement in this direction is then no longer possible, the motor 41 being able to be reactivated only after reversal of the direction of movement.

Figure 1B:
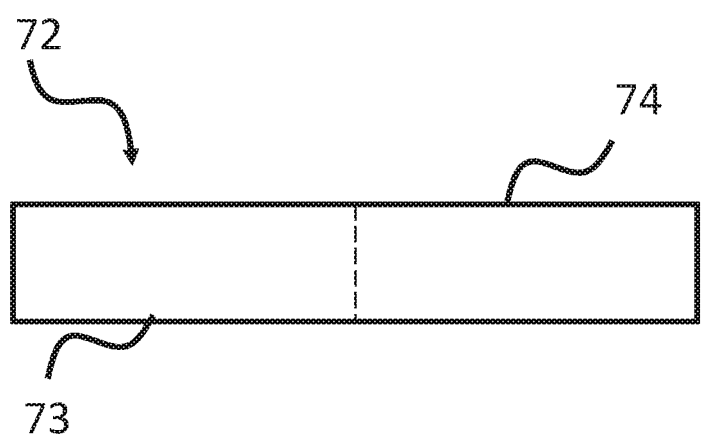
FIG. 1B shows a schematic a tension spring.

Through the traveling of the spindle nut 45 in the proximal direction, i.e. in the direction of the motor 41, a tension is applied to the traction means 50, whereby a sequential closing of the finger members 20, 30 is achieved by means of deflection at the deflecting element 60 and adjusted spring constants or stiffnesses of the resetting springs 15, 25. The mechanism can be implemented with two and also three finger members, wherein the configuration with two finger members, as is shown in FIG. 1, has the advantage of a natural finger length. With three finger members, a greater approximation to a natural finger function can be achieved. In some embodiments, at least one of the resetting springs 15, 25 is formed as a spring element with differing spring constants along its length. FIG. 1b schematically illustrates a spring element 72 that includes portions 73, 74 with different spring constants at locations along a length of the spring element 72.

The drive 40 itself may be arranged both in a finger member and also in the base; aside from the operation of the traction means 50 by means of the shown spindle drive with the spindle nut 45, it is also possible to roll the traction means 50 onto and back off of a roller. In addition to the illustrated embodiment, linear actuators and pneumatic or hydraulic cylinders or bellows may also be used as a drive.

By means of the invention, it is possible, with a simple kinematic with only one drive, to ensure a high gripping security through self-adjustment of the fingers to the form of the objects to be gripped, and to ensure a physiological gripping pattern in prosthetic fingers while gripping various objects. At a given friction coefficient of the item and the surface of the finger members, the gripping security is primarily dependent on the gripping strength and form fit with the object to be gripped. The present invention substantially increases the form fit independently of the geometry of the object to be gripped, as a sequential and complete application of both or all finger members is achieved.

Likewise, the embodiment of the invention offers the possibility of flexing the finger passively, which corresponds to a physiological behavior and which relieves the mechanical components. In handling in an unstructured environment, damage which results from collisions can be reduced. The possibility of passive flexion is particularly ensured by the displaceable deflection roller 60. The finger 1 can be directly used again in an impact load due to the resetting force via the tension spring 70. The illustrated embodiment represents a so-called underactuated system, in which the number of actuators is lower than the number of degrees of freedom. In kinematic coupling of the joints via the traction means, a member can bend even with a stationary drive while others are extended. Thus, the form fit is maintained even with changes or relocation of the gripped object.

Figure 3:
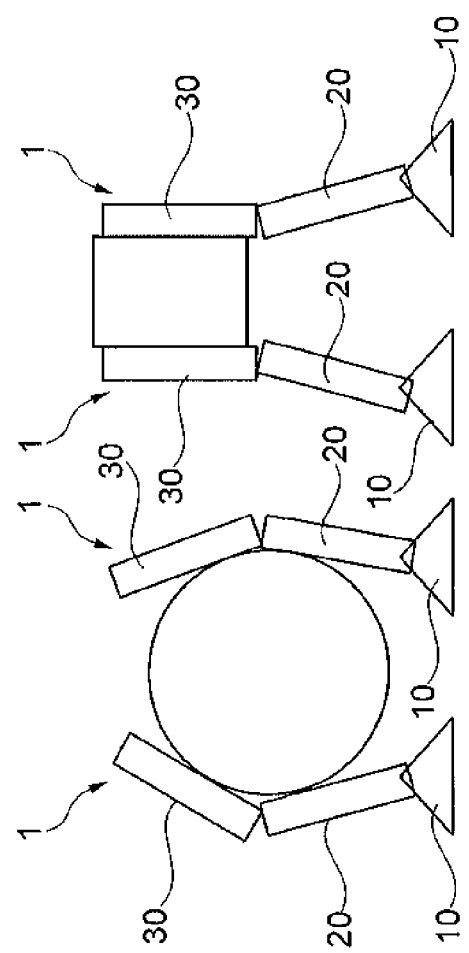
FIG. 3 shows gripping situations.

FIG. 3 shows two different gripping situations, as may occur for the fingers according to FIGS. 1, 2, 3a and 4. The left view shows the gripping of an object with a round cross section, the right view shows the gripping of an object with a polygonal, flat cross section.

The left view in FIG. 3 shows that, after a first contact of the first finger member 20, which is fixed on the base 10 in an articulated manner, the secondary member 30 is placed around the cross section of the object to be gripped, if the two bases 10 of the fingers 1 are closer together than the maximum diameter of the object to be gripped. The first finger members must then first be spread apart, so that they initially rest on the lower half of the object to be gripped. If the drive, not shown, is further actuated, the secondary members 30 are applied to the object and can hold this securely.

Another gripping situation is shown in the right view, in which the two fingers 1 with their bases 10 are further apart than the object to be gripped is wide, i.e. a gripping situation in which a narrow or flat object is to be gripped. The extension of the distal finger member or secondary member 30 beyond 0° or a starting position, which is called a hyperextension of the secondary members 30, offers the advantage of an adjustment to the form of the object and thereby to a greater contact area, whereby a more secure grip and a more physiological gripping pattern in prosthetics can be achieved.

If a member, in particular a secondary member 30, is stretched beyond its zero position, wherein the zero position is the resting position or the starting position in the non-actuated state, this is referred to as hyperextension. This hyperextension is advantageous when gripping flat objects, as is shown in the right of FIG. 3, because the tips of the secondary members 30 adjust to the object to be gripped. The individual finger members 20, 30 are coupled by the traction means 50, so that, even with a locked drive 40, the bending or flexion of one member 20, 30 is possible during simultaneous stretching or extension of other members of the artificial finger. Through the kinematic coupling of the joints between the respective members 20, 30, these effects can also occur, for example, during gripping, when the tips of the secondary member touch an object before the previous members. There is then a stretching or extension of the fingertip, while the remaining members further bend or flex.

By means of the arrangement of the deflection rollers 24, 60, 31 and the corresponding guide 21 of the traction means 50, it is possible to influence the equilibrium of forces between the finger members 20, 30 such that a force on the last member leads to a stretching, while the same force acts on the other members in the bending direction. Then, for example when gripping small, flat objects, the contact force which arises in the fingertip is converted into extension moments for the member of the fingertip, while at the same time this contact force is converted into bending moments for the previous members, i.e. those finger members which extend from the fingertips in the direction of the base 10.

Independent of a change in length of the traction means 50, a hyperextension of the last member or the last members arises here if the preceding member or members is bent at the same time.

In the use of springs for tensioning of the traction means 50, individual members may also be stretched, while others are blocked, as the length of the traction means 50 is increased and the path for the respective joint is thereby freed.

While hyperextension is desired in the gripping of flat objects, it is disadvantageous when grasping larger or rounded objects, as is shown in the left view of FIG. 3. As the fingers are underactuated, hyperextension cannot be actively influenced by separate drives. It is therefore provided that the kinematic arrangement of the deflection rollers 31, 60 is such that a switching point P is formed for effecting a hyperextension. The switching point P is that location, which is located for example near a fingertip, at which the effect of an external force leads either to a stretching or to a bending, depending on the position at which the external force acts. If the external force is applied at the end of the finger member away from the base, i.e. in the distal direction to the fingertip, this leads to a stretching of the joint and hyperextension. This is the case, for example, when gripping a thin flat object. If the force migrates in the direction of the base or in the proximal direction of the finger member, the stretching is then inhibited, whereas a bending of the member in question remains possible. It is thus also possible to actively grip objects with the last secondary member and to enclose an object with the finger.

The deflection rollers may be mounted displaceably and adjustably on the members, so that the switching point is freely selectable within certain limits. If certain of the deflection rollers are movably suspended, possibly against a spring force, the switching point may also be changed during the gripping action, depending on the forces in the traction means.

Figure 3A:
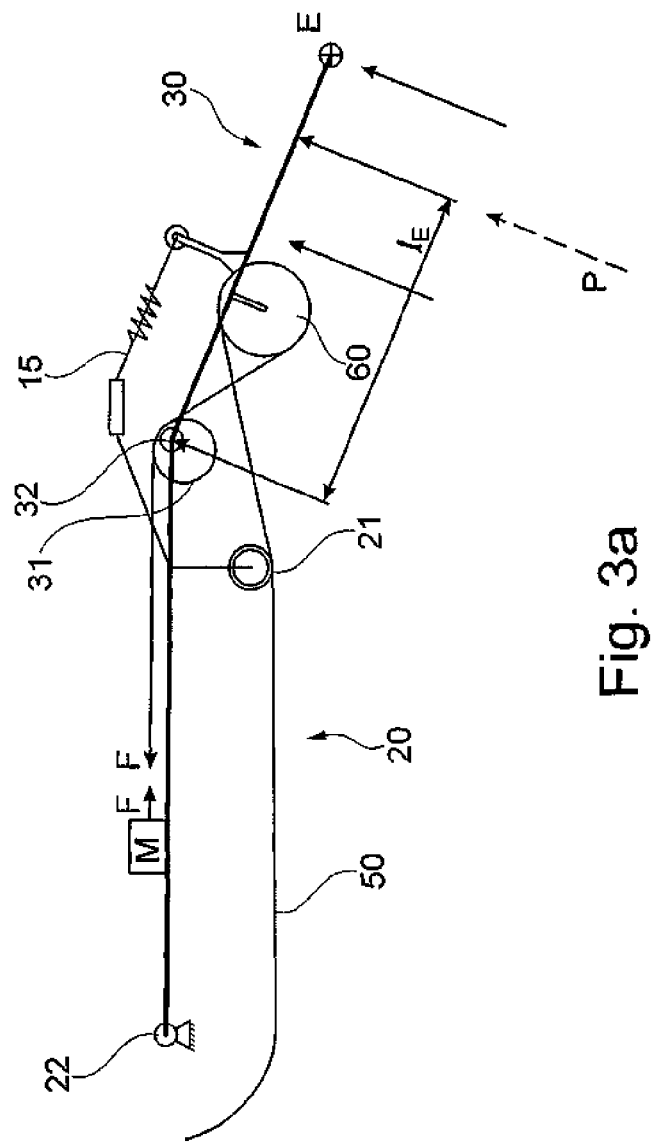
FIG. 3a shows a representation of a prosthetic finger with forces.

FIG. 3a shows a sketch of an artificial finger with a first member 20 and a secondary member 30, the basic construction of which corresponds to that of FIG. 1. Not all components of the finger of FIG. 1 are shown, for reasons of clarity. FIG. 3a shows the switching point P between an inhibited and a free hyperextension. If the force application point of an external contact force $F_E$ is arranged beyond the switching point P as seen from the pivot axis 32, the active lever IE extends and the stretching of the secondary member 30 is no longer inhibited, which leads to a hyperextension about the pivot axis 32. At the same time, a torque in the flexion direction is further formed in the first member 20 in the base joint about the pivot axis 22. If the force application point is located on the near side of the switching point P, i.e. closer to the pivot axis 32, an extension during application of tension to the traction means 50 is inhibited due to the kinematic arrangement of the deflection rollers, so that the finger 1 remains in the bent position shown. A hyperextension of the secondary member 30 cannot occur. If the deflection roller 60 is movably mounted on the secondary member 30, the switching point P can be changed; in a spring-loaded mounting of the deflection roller 60, a displacement of the switching point may occur depending on the tensile forces occurring in the traction means 50.

Figure 4:
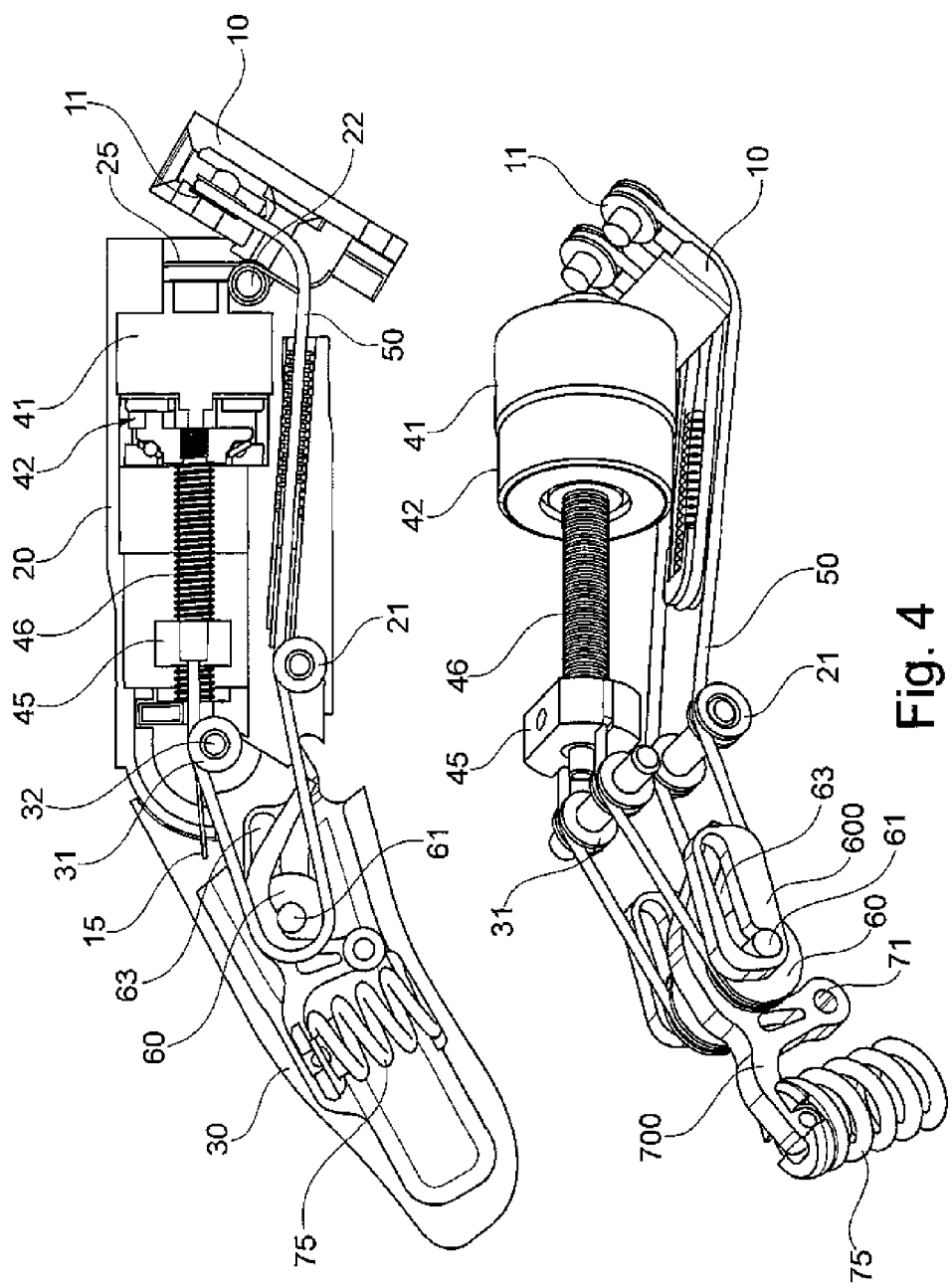
FIG. 4 shows a variant of the artificial finger.

FIG. 4 shows a mechanical concept of an artificial finger 1, which differs from that of FIG. 1. The basic construction with a base 10, a first finger member 20 mounted thereon in an articulated manner about a pivot axis 22, and a secondary member 30 mounted about the pivot axis 32, corresponds to the embodiment of FIG. 1. The spindle nut 45 is displaced along the longitudinal extent of the spindle 46 in the direction of the drive 41 or away therefrom by means of the drive 41, the gear 42 and the spindle 46. A change in the effective length of the traction means 50 according to the rotational direction and direction of displacement of the spindle nut 45 is effected via the traction means 50, which is guided over a plurality of deflection rollers 31, 60, 21, 11. If the spindle nut 45 is displaced in the direction of the drive 41, the effective length of the traction means 50 is shortened, and the secondary member 30 is flexed. The springs 25, 15 with varying spring stiffnesses are used to ensure the sequential applying of the respective finger members 20, 30 to the object to be gripped.

The deflection roller 60 is mounted in a slot guide 63, which is designed as an elongated hole guide, about the rotational axis 61, around which protruding pins are formed on both sides. The elongated hole guide 63 is formed in a frame 600; two frames are arranged on both sides of the parallel-guided traction means 50 and receive the pins of the deflection roller 60. The slot guide 63 has a front or distal portion, in which the pins of the deflection roller 60 are mounted in a starting position. A bevel leads from this front region, which bevel is guided at an angle of approximately 70° to the force direction K to a sliding portion, which is substantially oriented in the force direction K. The deflection roller 60 is held with the pins in the front region via a two-armed lever 700, which is oriented about a pivot axis 71 parallel to the rotational axis 61 of the deflection roller 600. The lever arm facing away from the deflection roller 60 is supported via a compression spring 75 and presses the pins of the deflection roller 60 into the slot guide 63.

Figure 5:
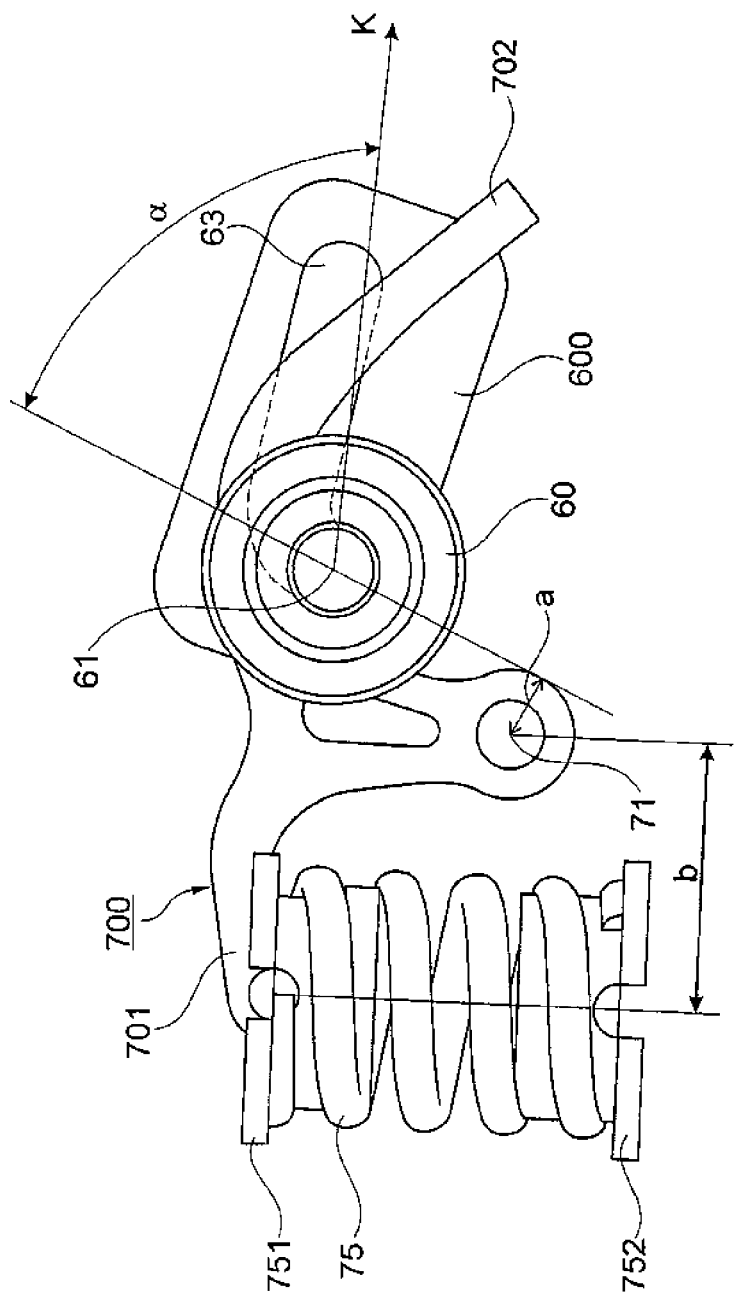
FIG. 5 shows a detailed view of the overload protection in the starting position.

The operation of this overload construction is explained in detail with reference to FIGS. 5 and 6. FIG. 5 is an enlarged detail view showing the arrangement of FIG. 4 in the starting position. The compression spring 75 is supported via a lower plate 752 on the secondary member, not shown, and via an upper plate 751 on a first lever arm 701 of the double lever 700. The double lever 700 is loaded via the compression spring 75 in the clockwise direction about the pivot axis 71, so that the deflection roller 60 is pressed into the front portion of the slot guide 63 via the second lever arm 702, which has a curved contour facing the deflection roller 60. The front portion allows a displacement of the deflection roller 60 along a bevel, which has an inclination angle to the force direction K, wherein the force direction K is determined by the guiding of the traction means 50, not shown, and the arrangement of the corresponding deflection rollers 21, 31. In the illustrated embodiment, the angle is approximately 70°; depending on the inclination of the bevel and the increase or decrease of the inclination angle, greater forces are necessary in the force direction K, in order to build up a force component perpendicular to the force direction K, so that the deflection roller 60 slides along in the front portion. By means of the bevel, the double lever 700 and the bent contour of the second lever arm 702, a force intensification of the pressure force of the compression spring 75 is yielded, which means that a relatively short compression spring 75 may be chosen in order to provide sufficiently high holding forces for the deflection roller 60 as an overload protection. In addition, due to the possible lever geometries, the spring path of the compression spring need not be very great since, due to the angle between the force direction K and the orientation of the bevel in the first portion, a large part of the force arises through the friction of the slot guide 63, and only a small portion of the force need be applied through the pre-tensioned compression spring 75.

The pre-tensioning force of the compression spring 75 is also increased by the provided lever ratios. The ratio of the first force lever a between the pivot axis of the double lever 700 and the displacement direction of the deflection roller along the front portion of the slot guide to the second force lever b between the point of entry of the pressure force into the first lever arm 701 and the pivot axis 71 of the double lever is 1:4 in the embodiment shown, so that a four-fold power transmission can be exerted on the rotation axis 61 of the deflection roller. The pivot axis 71 of the double lever 700 is lower than the rotation axis 61 of the deflection roller 60 in the front portion of the slot guide 63, whereby it is ensured in addition to the force transmission that only a small spring path is necessary to enable a large displacement path in the slot guide. In addition to the low-lying center of rotation of the pivot axis 71, the second lever arm 702 has a sloped contour which ensures that, in each displacement point of the rotation pins of the deflection roller 60, a defined friction angle $\beta$ is provided.

Figure 6:
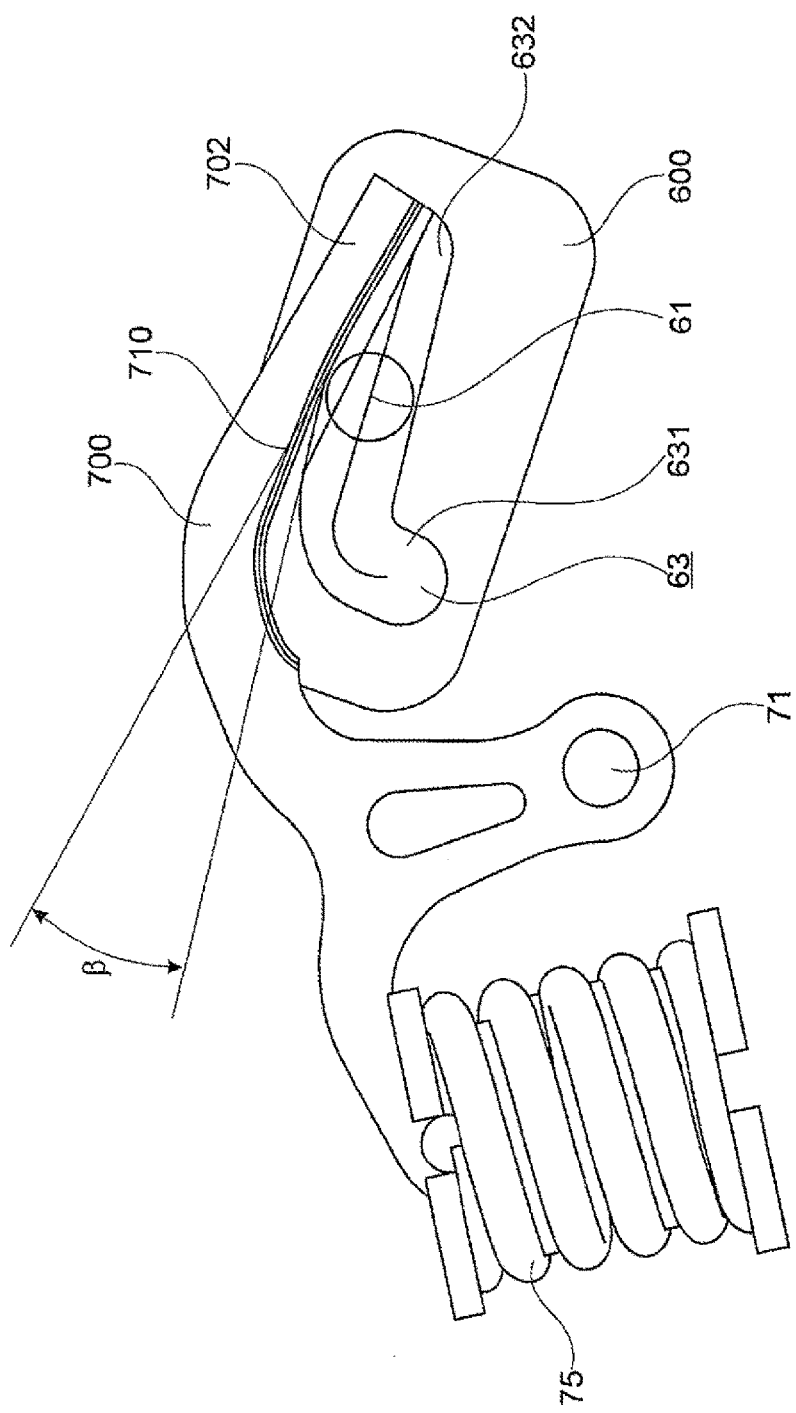
FIG. 6 shows an overload protection according to FIG. 5 in an operating position.

FIG. 6 shows the friction angle $\beta$ between the lower contour 710 of the second lever arm 702 in the already displaced state of the deflection roller 60, not shown, within the slot guide 63. In this illustration, the front portion 631 with inclined orientation to the force direction K and the sliding portion 632 within the frame 600 can be seen. The indicated bearing pin of the deflection roller 60 with the rotational axis 61 is located approximately in the center of the sliding portion 632; a friction angle $\beta$ is formed between the inner contour 710 in the application point of the second lever 702 and the extent of the slot guide 63 due to the curved contour 710, which friction angle $\beta$ is necessary to ensure that, after removal of the overload, the deflection roller 60 and the secondary member 30 are moved back into the starting position. For this purpose, the chosen friction angle $\beta$ is sufficiently large, 12° in the illustrated embodiment, which is sufficient, upon removal of the overload, to effect a force component counter to the force direction K and along the path of motion of the bearing pins of the deflection roller 60 within the slot guide 63 by means of the pressure from the compressed compression spring 75 via the first lever arm 701 about the pivot axis 71. The friction angle $\beta$ may be constant over the length of the second lever arm 702; alternatively, the contour 710 may form an increasing or decreasing friction angle $\beta$, in order to achieve a desired resetting behavior. After removal of the overload, a force component in the direction of the front portion 631 is exerted through the choice of the friction angle $\beta$ in order to effect the resetting.

The illustrated embodiment of the overload protection according to FIGS. 4 to 6 has the effect that, when an overload force is reached, a sudden release of the mechanism occurs, as a result of which the gripping strength applied by the finger 1 is abruptly reduced. Once the applied flexion force diminishes or is completely removed, the deflection roller 60 is moved back again to the starting position according to FIG. 5.

The invention claimed is:

1. An artificial finger for prosthetics and gripping technology, comprising:
a base;
a first finger member mounted on the base in an articulated manner;
a secondary member mounted on the first finger member in an articulated manner;
a drive for adjusting the secondary member relative to the first finger member and the first finger member relative to the base;
a deflection member displaceably mounted to at least one of the first finger member and the secondary member and biased against displacement when the drive is operated;
a traction member coupled to the drive and guided on the deflection member;
a first reset element provided for resetting the first finger member relative to the base and a second reset element for resetting the secondary member relative to the first finger member, and the first finger member is acted upon with a resetting force from the first reset element which differs from a resetting forcing acting upon the secondary member from the second reset element;
wherein moving a position of the deflection member along the length of the artificial finger adjusts a position of a point arranged on at least one of the first finger member and the secondary member, wherein application of an external force resulting from grasping an object using the artificial finger leads to either a flexion movement or a hyperextension movement of the secondary member relative to the first finger member depending on a location of the object along a length of the artificial finger distal or proximal of the point, and depending on at least one of a size of the object and a shape of the object.

2. The artificial finger as claimed in claim 1, wherein the first reset element is formed as a spring element with differing spring constants over a length of the spring element.

3. The artificial finger as claimed in claim 1, wherein the second reset element includes a first resetting spring providing the secondary member with resetting forces in relation to the first finger member, and the first resetting element includes a second resetting spring providing the first finger member with resetting forces in relation to the base in a direction of a starting position, wherein spring constants of the resetting springs are different.

4. The artificial finger as claimed in claim 3, wherein the spring constant of the first resetting spring is greater than the spring constant of the second resetting spring.

5. The artificial finger as claimed in claim 1, wherein the traction member is guided below a pivot axis of the secondary member.

6. The artificial finger as claimed in claim 1, wherein the deflection mechanism is mounted displaceably or pivotably on the secondary member.

7. The artificial finger as claimed in claim 1, wherein a pre-tensioning force is applied to the traction member in a distal direction.

8. The artificial finger as claimed in claim 1, wherein the drive is formed as a self-locking linear drive or a non-locking pneumatic drive.

9. The artificial finger as claimed in claim 1, wherein the drive has a reduction gear, which is coupled to a roller or a spindle drive on which the traction member is fixed.

10. The artificial finger as claimed in claim 1, wherein the drive is arranged in the first finger member or the secondary member.

11. The artificial finger as claimed in claim 1, wherein the deflection member comprises a roller or a pin.

12. An artificial finger for prosthetics and gripping technology, comprising:
- a base;
- a first finger member mounted on the base in an articulated manner;
- a secondary member mounted on the first finger member in an articulated manner;
- a drive to adjust the secondary member relative to the first finger member and the first finger member relative to the base;
- at least one reset element operable to reset the first finger member relative to the base and the secondary member relative to the first finger member;
- a point on the first or second finger member at which application of an external force resulting from grasping an object using the artificial finger leads to either a flexion movement or a hyperextension movement of the secondary member relative to the first finger member depending on a location of the object along a length of the artificial finger distal or proximal of the point, and depending on at least one of a size of the object and a shape of the object;
- a deflection mechanism carried by and displaceably mounted relative to the secondary member, the deflection mechanism being biased against displacement when the drive is operated;
- a traction member coupled to the drive and fixed on the base, the traction member being supported by the deflection mechanism;
- wherein movement of the deflection member along the length of the artificial finger adjusts a position of the point.

13. The artificial finger as claimed in claim 12, wherein the at least one reset element is formed as a spring element with differing spring constants over a length of the spring element.

14. The artificial finger as claimed in claim 12, wherein the at least one reset element includes a first resetting spring configured to provide the secondary member with resetting forces in relation to the first finger member, and a second resetting spring configured to provide the first finger member with resetting forces in relation to the base in a direction of a starting position, wherein spring constants of the resetting springs are different.

15. The artificial finger as claimed in claim 14, wherein the spring constant of the first resetting spring is greater than the spring constant of the second resetting spring.

16. An artificial finger for prosthetics and gripping technology, comprising:
- a base;
- a first finger member mounted on the base in an articulated manner;
- a secondary member mounted on the first finger member in an articulated manner;
- a drive to adjust the secondary member relative to the first finger member and the first finger member relative to the base;
- a first reset element to reset the first finger member relative to the base, and a second reset member to reset the secondary member relative to the first finger member;
- a deflection roller carried by and displaceably mounted relative to the secondary member, the deflection roller biased against displacement when the drive is operated;
- a traction member coupled to the drive and supported by the deflection roller
- wherein moving a position of the deflection roller along the length of the artificial finger adjusts a position of a point arranged on at least one of the first finger member and the secondary member, and application of an external force to the artificial finger resulting from grasping an object using the artificial finger leads to either a flexion movement or a hyperextension movement of at least one of the first finger member and the secondary member depending on a location of the external force relative to the point, and hyperextension movement occurs depending on at least one of a size of the object, a shape of the object, and a location of the object relative to the first finger member and the secondary member.

17. The artificial finger as claimed in claim 16, wherein the first reset element applies a different resetting force to the first finger member than the second reset element applies to the secondary member.

* * * * *